US007270991B2

(12) United States Patent
Williamson et al.

(10) Patent No.: US 7,270,991 B2
(45) Date of Patent: Sep. 18, 2007

(54) EXPRESSION SYSTEM

(75) Inventors: Ethel Diane Williamson, Salisbury (GB); Leslie William James Baillie, Salisbury (GB); Julie Miller, Salisbury (GB)

(73) Assignee: The Secretary of State for Defense, Salisbury, Wirthshire (GB)

( * ) Notice: Subject to any disclaimer, the term of this patent is extended or adjusted under 35 U.S.C. 154(b) by 0 days.

(21) Appl. No.: 10/483,150

(22) PCT Filed: Jul. 9, 2002

(86) PCT No.: PCT/GB02/03166

§ 371 (c)(1),
(2), (4) Date: Jun. 25, 2004

(87) PCT Pub. No.: WO03/006649

PCT Pub. Date: Jan. 23, 2003

(65) Prior Publication Data

US 2004/0235140 A1    Nov. 25, 2004

(30) Foreign Application Priority Data

Jul. 10, 2001    (GB) .................... 0116798.0

(51) Int. Cl.
*C12N 1/20*    (2006.01)
*A61K 35/00*    (2006.01)
(52) U.S. Cl. .................... 435/252.1; 424/93.1
(58) Field of Classification Search ............... 530/350; 435/221, 220, 252.35, 832, 69.1; 536/23.2, 536/23.1
See application file for complete search history.

(56) References Cited

U.S. PATENT DOCUMENTS

| | | | |
|---|---|---|---|
| 5,036,002 A | | 7/1991 | Hastrup |
| 5,620,880 A | | 4/1997 | Sloma et al. |
| 5,891,701 A | * | 4/1999 | Sloma et al. ............ 435/221 |
| 5,958,728 A | | 9/1999 | Adams |

FOREIGN PATENT DOCUMENTS

| | | |
|---|---|---|
| EP | 0 492 274 A2 | 7/1992 |
| GB | 2 331 523 A | 5/1999 |
| WO | WO 97/03185 | 1/1997 |

OTHER PUBLICATIONS

He et al., The protease genes of *Bacillus subtilis*, Jun. 1991, Res. Microbio., vol. 142, pp. 797-803.*
Lee, JW and Parulekar SJ, Enhanced production of alpha amylase in the fed batch culture of *B. subtilis* TN106, Biotechol. bioeng. 42: 1142-1150.*
Baillie, et al., "The expression of the protective antigen of *Bacillus anthracis* in *Bacillus subtilis*," *Journal of Applied Microbiology*, 84:741-746 (1998).

Baillie, et al., "Evaluation of *Bacillus subtilis* strain IS53 for the production of *Bacillus anthracis* protective antigen," *Letters in Applied Microbiology*, 19:225-227 (1994).
Baillie, et al., "Development of a *Bacillus subtilis* based system for the expression of the protective antigen of *Bacillus anthracis*," In *Proceedings of the International Workshop on Anthrax*, Winchester, UK *Salisbury Medical Bulletin*-Special Supplement No. 87, Sep. 19-21, 1995, pp. 133-135 (1996).
Belton, et al., "Studies on a Protective Antigen Produced *In Vitro* From *Bacillus anthracis*: Medium and Methods of Production," *British Journal of Experimental Pathology*, 35:144-152 (1954).
Coote, "Sporulation in *Bacillus subtilis*, Characterization of Oligosporogenous Mutants and Comparison of Their Phenotypes with Those of Asporogenous Mutants," *Journal of General Microbiology*, 71:1-15 (1972).
Coulson, et al., "*Bacillus anthracis* protective antigen, expressed in *Salmonella typhyimurium* SL 3261, affords protection against anthrax spore challenge," Vaccine, 15:1395-1401 (1994).
Driks, "*Bacillus subtilis* Spore Coat," *Microbiology and Molecular Biology Reviews*, 63(1):1-20 (1999).
Errington, "*Bacillus subtilis* Sporulation: Regulation of Gene Expression and Control of Morphogenesis," *Microbiological Reviews*, 57(1):1-33 (1993).
Fort, et al., "Nucleotide Sequence of Sporulation Locus *spoIIA* in *Bacillus subtilis*," *Journal of General Microbiology*, 130:2147-2153 (1984).
Guerout-Fleury, et al., "Antibiotic-resistance cassettes for *Bacillus subtilis*," Gene, 167:335-336 (1995).
Hambleton, et al., "Anthrax: the disease in relation to vaccines," Vaccine, 2:125-132 (1984).
Harwood, et al., Appendix 1—Media, Molecular Biological Methods for *Bacillus*, 545-550 (1990), Harwood, et al. Cutting (editors, Wiley, Chichester UK).
Hoch, "*spo0* Genes, the Phosphorelay, and the Initiation of Sporulation," In *Bacillus* (Editors Sonenshein, A.L., et al., Chapter 51: 747-755 ( ), American Society for Microbiology, Washington, D.C.
Higuchi, et al., "A general method of in vitro preparation and specific mutagenesis of DNA fragments: study of protein and DNA interactions," *Nucleic Acids Research*, 16(15):7351-7367 (1988).
Iacono-Connors, et al., "Expression of the *Bacillus anthracis* Protective Antigen Gene by Baculovirus and Vaccinia Virus Recombinants," *Infection and Immunity*, 58(2):366-372 (1990).
Ivins, et al., "Cloning and Expression of the *Bacillus anthracis* Protective Antigen Gene in *Bacillus subtilis*," *Infection and Immunity*, 54(2):537-542, (Nov. 1986).

(Continued)

*Primary Examiner*—Robert B. Mondesi
(74) *Attorney, Agent, or Firm*—Kilpatrick Stockton LLP

(57) ABSTRACT

A recombinant microorganism comprises an asporogenic *Bacillus subtilis* strain in which a gene encoding a protease enzyme has been downregulated or inactivated. In particular sigma factorspoIIAC is inactivated such that the strain is asporogenic. These strains are particularly useful as expression vehicles for proteins such as protective antigen (PA) of *Bacillus anthracis*.

20 Claims, 2 Drawing Sheets

OTHER PUBLICATIONS

Figure 1:
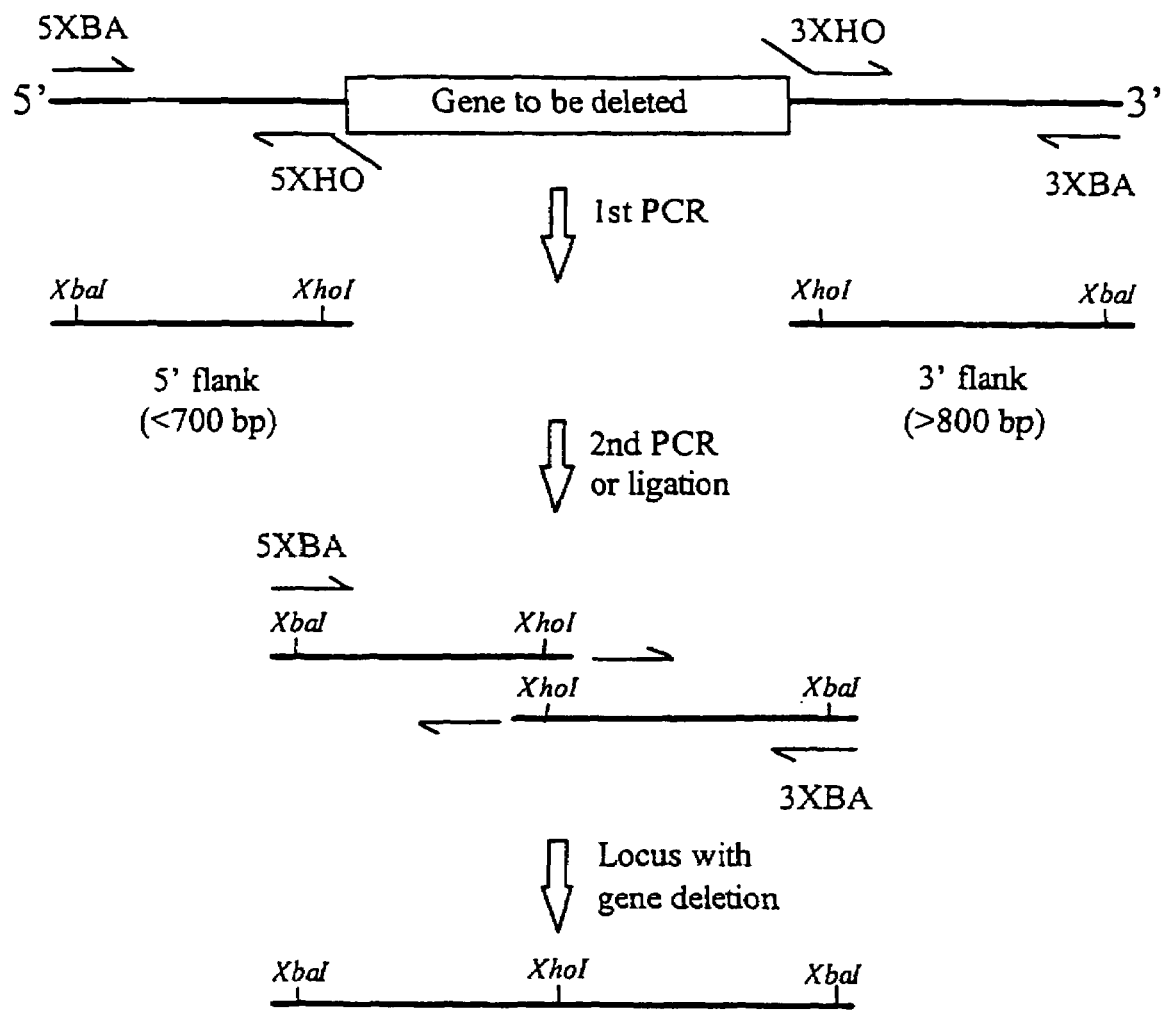

Kunst, et al., "The complete genome sequence of the Gram-positive bacterium *Bacillus subtilis,*" *Nature*, 390(20):249-256 (1997).

Leenhouts, et al., "A general system for generating unlabelled gene replacements in bacterial chromosomes," *Mol. Gen. Genet.*, 253:217-224 (1996).

Lewis, et al., "σ factors, asymmetry, and the determination of cell fate in *Bacillus subtilis,*" *Proc. Natl. Acad. Sci.*, 91:3849-3853 (1994).

Lipman, et al., "Rapid and Sensitive Protein Similarity Searches," *Science*, 1435-1441 (1985).

Losick, et al., "Genetics of Endospore Formation in *Bacillus subtilis,*" *Ann. Rev. Genet.*, 20:625-69 (1986).

McBride, et al., "Protective efficacy of a recombinant protective antigen against *Bacillus anthracis* challenge and assessment of immunological markers," *Vaccine*, 16(8):810-817.

Miller, et al., "Production and purification of recombinant protective antigen and protective efficacy against *Bacillus anthracis,*" *Letters of Applied Microbiology*, 26:56-60 (1998).

Oh, Hee-Bok, "Expression and Secretion of *Bacillus anthracis* Protective Antigen in *Bacillus brevis,*" *3rd International Conference on Anthrax*, University of Plymouth, Sep. 7-10, 1998 (Abstract).

Partridge, et al., "The role of σ$^F$ in prespore-specific transcription in *Bacillus subtilis,*" *Molecular Microbiology*, 5(3):757-767 (1991).

Singh, et al., "Internationalization and Processing of *Bacillus anthracis* Lethal Toxin by Toxin-sensitive and -resistant Cells," *The Journal of Biological Chemistry*, 264(19):11099-11102 (1989).

Stephenson, et al., "Cellular lysis in *Bacillus subtilis*; the affect of multiple extracellular protease deficiencies," *Letters in Applied Microbiology*, 29:141-145 (1999).

Sun, et al., "Identification of a new σ-factor involved in compartmentalized gene expression during sporulation of *Bacillus subtilis,*" *Genes & Development*, 3:141-149 (1989) Cold Spring Harbor Laboratory.

Thwaite, et al., "Optimization of the Cell Wall Microenvironment Allows Increased Production of Recombinant *Bacillus anthracis* Protective Antigen from *B. subtilis,*" *Applied and Environmental Microbiology*, 68(1):227-234 (2002).

Turnbull, "Anthrax Vaccines : Past, Present and Future," *Vaccine*, 9 :533-539 (1991).

Vodkin and Leppis, "Cloning of the Protective Antigen Gene of *Bacillus anthracis,*" *Cell*, 34:693-697 (1983).

Waites, et al., "Sporulation in *Bacillus subtilis,*" *Biochem. J.*, 118:667-676 (1970).

Welkos, et al., "Sequence and analysis of the DNA encoding protective antigen of *Bacillus anthracis,*" *Gene*, 69:287-300 (1988).

Wu, et al., "Engineering a *Bacillus subtilis* Expression-Secretion System with a Strain Deficient in Six Extracellular Proteases," *Journal of Bacteriology*, 173(16):4952-4958 (1991).

* cited by examiner

SEQUENCE LISTING

<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
gcttctagat gaagccaata ttccg                                         25

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 2
tatacctaaa tagagctcca tacctgcttc ttttatttgt cag                     43

<210> SEQ ID NO 3

```
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 3
gaagcaggta tggagctcta tttaggtata tcatctctcg c                    41

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
aagtctagaa ataacgttga cattc                                      25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
tcctctagaa acatcactgg aggac                                      25

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 6
tctgcttaat ttctcgagaa catcgctgta tattaactgt ag                   42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 7
tactgcgatg ttctcgagaa attaagcaga tttccctgaa aa                   42

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
gcttctagat ggcttccaat gggtc                                      25

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 9
```

```
acctctagat ttcggttgaa aacaag                                          26

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 10
agtatgaaaa gcctcgagga aattttccaa atgaatttgt aag                       43

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 11
ttggaaaatt tcctcgaggc ttttcatact attgctatac ag                        42

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
tgttctagac acgaggtcga gcatt                                           25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
atttctagag ccgatcggtc atgtgc                                          26

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 14 cccccttagca tcctcgaggt ttctgattct tatgataaaa c                        41

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 15
agaatcagaa acctcgagga tgctaagggg ctgccggtcg aag                       43

<210> SEQ ID NO 16
<211> LENGTH: 25
<212> TYPE: DNA
```

<213> ORGANISM: Artificial Sequence
<220> FEATURE:
<223> OTHER INFORMATION: Description of Artificial Sequence: Primer

<400> SEQUENCE: 16
ccgtctagat gtgccgtcca agtcc                                    25

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
gactctagac atctgccgct ggcttg                                   26

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 18 tgttttgtt tgctcgagat atttcgctct gcccttcttt ttc                 43

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 19
agagcgaaat atctcgagca aacaaaaaca gtcaggacac ag                 42

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
cgatctagaa ttcgaagatg cagtc                                    25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 21
gaatctagaa agtatccagt cccgc                                    25

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 22
ttttgttgag tactcgagac agaaaaccgc tcctgatttg c                  41

```
<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 23
gcggttttct gtctcgagta ctcaacaaaa actaacataa c                           41

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
gcatctagac aagcagtccg ataatc                                            26
```

EXPRESSION SYSTEM

CROSS REFERENCE TO RELATED APPLICATIONS

This application is the U.S. national phase of International Application No. PCT/GB02/03166 filed on Jul. 9, 2002 and published in English as International Publication No. WO 03/006649 A2 on Jan. 28, 2003, which application claims priority to Great Britain Application No. 0116798.0 filed on Jul. 10, 2001, the contents of which are incorporated by reference herein.

The present invention relates to an expression system, useful in the production of a range of proteins, which is derived from *B. subtilis*. In addition, the invention relates to the use of this system in the production of proteins such as antigens used in vaccines, for example recombinant Protective Antigen (PA) of *Bacillus anthracis*.

The protective antigen (PA) of *Bacillus anthracis*, the causative agent of anthrax, is the key component of the current UK human anthrax vaccine (Hambleton, P. et al., (1984) Anthrax: the disease in relation to vaccines. Vaccine 2;125-132). Due to safety concerns relating to the handling of *B. anthracis* attempts have been made to express PA from a variety of different hosts. These include attenuated strains of *B. anthracis* (Belton, F. C. et al., (1954) British Journal of Experimental Pathology, 35;144-152 and Turnbull, P. C. B. (1991) Vaccine 9,533-539), *B. subtilis* (Ivins, B. E. et al., Infection and Immunity (1986), 54;537-542, Baillie, L. W. J. et al., (1994) Letters in Applied Microbiology 19;225-227, Baillie, L. W. J., et al., (1996) In Proceedings of the International Workshop on Anthrax, 19-21 Sept 1995, Winchester, UK. Salisbury Medical Bulletin 1996, 87 (Special Suppl.) 133-135 and Baillie, L. W. J., et al., (1998) Journal of Applied Microbiology 84;741-746, *B. brevis* (Oh, H-B., et al., (1998) Abstracts of the 3rd International Conference on Anthrax, 7-10the Sept, 1998), vaccinia (Iancono-Connors, L. C., et al., (1990) Infect. Immun. 58;366-372), baculovirus (Iancono-Connors, L. C., et al., (1990) Infect. Immun. 58;366-372), *Salmonella typhimurium* (Coulson N. M. et al., Vaccine (1994) 12;1395-1401) and *E. coli* (Singh, Y. et al., (1989), J. Biol. Chem., 264;11099-11102 and Vodkin M. H. et al., (1993) Cell, 34;693-697).

While none of these systems is ideal, to date, the best yields have been achieved using *Bacillus* spp. *Bacillus* spp. have a history of safe use in both food and industry. A number of products from *Bacillus* spp. are generally recognised as safe for specific uses by the U.S. Food and Drug Administration. These products include enzymes for food processing as well as whole foods produced from the microorganism (*B. subtilis natto*).

The PA gene is expressed well in *B. subtilis* achieving levels of expression higher than those obtained with the current *B. anthracis* based system (Ivins, B. E. et al., (1986), supra.). In addition the protein is exported into the culture supernatant, simplifying subsequent purification protocols (Miller, J. et al., (1998) Letters in Applied Microbiology, 26;56-60).

A draw back of using bacilli is their ability to produce degradative proteases (Baillie, L. W. J. et al., (1994) supra.) and resistant spores (Driks, A. (1999) Microbiology and Molecular Biology Reviews 63;1-20).

Strains of *B. subtilis* have been engineered to overcome the problem of proteolytic degradation of expressed proteins. WB600 is one such a strain (Xu-Chu, Wu et al., (1991) Journal of Bacteriology. 173,4952-4958).

Using this strain a high level laboratory scale, expression and purification system, has been developed for the production of pure rPA. (Miller, J. et al., (1998) Letters in Applied Microbiology, 26;56-60).

In animal studies rPA invoked total protection to aerosol challenge with spores of a vaccine resistant strain of *Bacillus anthracis* (McBride, B. W., et al., (1998) Vaccine 16;8,810-817).

The ability of the production strain WB600 to form resistant spores raises the possibility of environmental contamination when the strain is grown to large numbers such as is the case with fermenters. This potential is of particular concern to industry who cannot risk cross-contamination with other products. Therefore, such systems require the use of a dedicated production plant.

Spore formation is regulated by a complex network of genes which function as a cascade (Hoch, J. A. spoo Genes, the phosphorelay, and the Initiation of sporulation. In *Bacillus* and other Gram-positive bacteria. Editors Sonenshein, A. L. et al., chapter 51;747-755, American Society for Microbiology, Washington D.C.). Targeted inactivation of early sporulation genes, such as spo0A, will result in a strain incapable of forming spores. Sporulation deficient strains in which the early sporulation genes spOA are deficient, may be physiologically compromised. Consequently, the effects of other genetic modifications may not be tolerated and strains may become non-viable.

The applicants have found however that strains of *B. subtilis* can be produced which are asporogenic and also protease deficient.

The present invention provides a recombinant microorganism comprising an asporogenic strain of *Bacillus subtilis* in which at least one gene which encodes a protease enzyme has been downregulated or inactivated.

Strains of this type provide good yields of heterologous proteins which the strain may be engineered to express, and do not generate problems associated with sporulation.

Suitable protease enzyme genes within the *B. subtilis* strain which may be inactivated or downregulated include serine alkaline protease E (subtilisin 1143 bp) (aprE), bacillopeptidase F (bpr), extracellular serine protease (epr) (1935 bp), extracellular metalloprotease (mpr) (939 bp), extracellular neutral protease (nprB) (614 bp) and extracellular neutral metalloprotease (nprE) (1563 bp).

The sequences of these genes can be determined from the literature (see in particular Kunst et al. Nature (1997) 390:249-256).

Preferably more than one, more preferably at least 3 and most preferably all of these genes are inactivated.

Inactivation or downregulation of the target sequence may be carried out using any of the known methods. For example, the sequence may be partially or totally deleted, and additionally may be subject to allelic replacement, or may be subjected to mutation including insertional mutation in order to inactivate the encoded protease enzyme. Alternative methods of gene inactivation such as the use of sense or antisense RNA constructs in order to prevent transcription of the gene sequence may also be employed.

In particular, the strain is rendered asporogenic by the inactivation of a sequence encoding sigma factor spoIIAC. The applicants have found that by inactivating this specific fragment of a stage II sporulation gene, stable asporogenic recombinant strains are produced which are robust and are particularly useful in the production of vaccines.

The spoIIA gene is one of the nine known stage-II loci. Mutation of this gene can block development at the septation stage of sporulation (Losick et al. supra.). This gene has been cloned and sequenced and found to be transcribed as a polycistronic unit of three cistrons encoding proteins of 13, 16 and 29 kd. These are encoded by regions designated spOIIAA, spoIIAB and spoIIAC respectively.

The sequence encoding sigma factor spoIIAC is suitably inactivated using the methods described above in relation to the inactivation or downregulation of the protease enzyme genes. Preferably however, the nucleic acid sequence encoding sigma factor spoIIAC within the Bacillus subtilis genome is partially or totally deleted, and optionally replaced with a different sequence. This different sequence may comprise, for example a marker gene, such as an antibiotic resistance gene, which will assist in the transformation process in selecting transformed clones.

Other regions of the spoIIA gene may also be deleted if desired.

In a particular method, the 5' and 3' regions flanking the target sequence to be deleted are amplified from B. subtilis chromosomal DNA in two separate reactions. A first amplification reaction (for example a polymerase chain reaction (PCR) reaction) is carried out using 5XBA-5XHO and 3XHO-3XBA primer pairs. The two amplified flanks are then used to self-prime each other and generate the locus minus the target sequence. This truncate can then be amplified by external primers in a second amplification (PCR) reaction.

Alternatively, the two flanking products from the first reaction may be cut with a suitable restriction endonuclease for example XhoI, mixed and ligated. Suitably, the primers are designed such that the 5'flank amplicon is up to 700 base pairs in length whilst the 3' flank is 800 or more base pairs in length. This allows clear identification of the ligation for example using gel chromatography. When the product of the ligation is run on a gel, three bands will be obtained. The target band will be of the order of 1.5 kbases in length.

This scheme is illustrated diagrammatically in FIG. 1 hereinafter

The ligation obtained in this way, or the product of the second PCR reaction forms the deleted locus which can then be used to form a suitable deletion plasmid. For example, the deleted locus may be cut with a restriction enzyme such as XbaI and cloned into pUC18. Suitable hosts such as E. coli DH5α can be used as the host for the initial cloning although TG90, which replicates high-copy number plasmids at low copy number, may be useful in some instances.

This is then subcloned into a suitable plasmid to form a deletion plasmid.

A particularly suitable plasmid is pOR120 (see FIG. 2), which has been shown to work effectively in B. subtilis (Leehouts et al, 1996, Mol. Gen. Genet. 253:217-224) and will allow unlabelled gene deletions or replacements to be made in bacterial chromosomes. It is derived from the lactococcal plasmid pWV)1, which lacks the repA gene (replication initiation protein), so will only replicate in strains expressing PepA in trans, such as E. coli EC1000. It contains the tetracycline resistance gene (tet) to enable selection of recombinants and the β-galactosidase gene (lacZ) to allow identification of revertants by blue/white selection. The lacZ is under the control of a p32 promoter (allowing expression in both gram-positive and gram-negative bacteria).

The deletion locus can then be subcloned into the pORI240 plasmid and transformants selected in a suitable host strain such as E. coli EC1000 by tetracycline resistance. Strains of B. subtilis and preferably strains of known provenance such as B. subtilis 168 can then be transformed using this plasmids, and transformants selected on tetracycline. (B. subtilis 168 is the strain used in the complete genome sequencing project [see Kunst et al. supra.] and can be obtained from the Institut Pasteur (CIP no. 106309). However, Bacillus subtilis WB600 may also be improved using this method.

The plasmid is unable to replicate in this strain, so transformants will have undergone chromosomal integration.

Then a second recombination event (resolving the cointegrant) which will yield white colonies with X-gal present (integrants will remain blue) can be readily selected.

Figure 2:
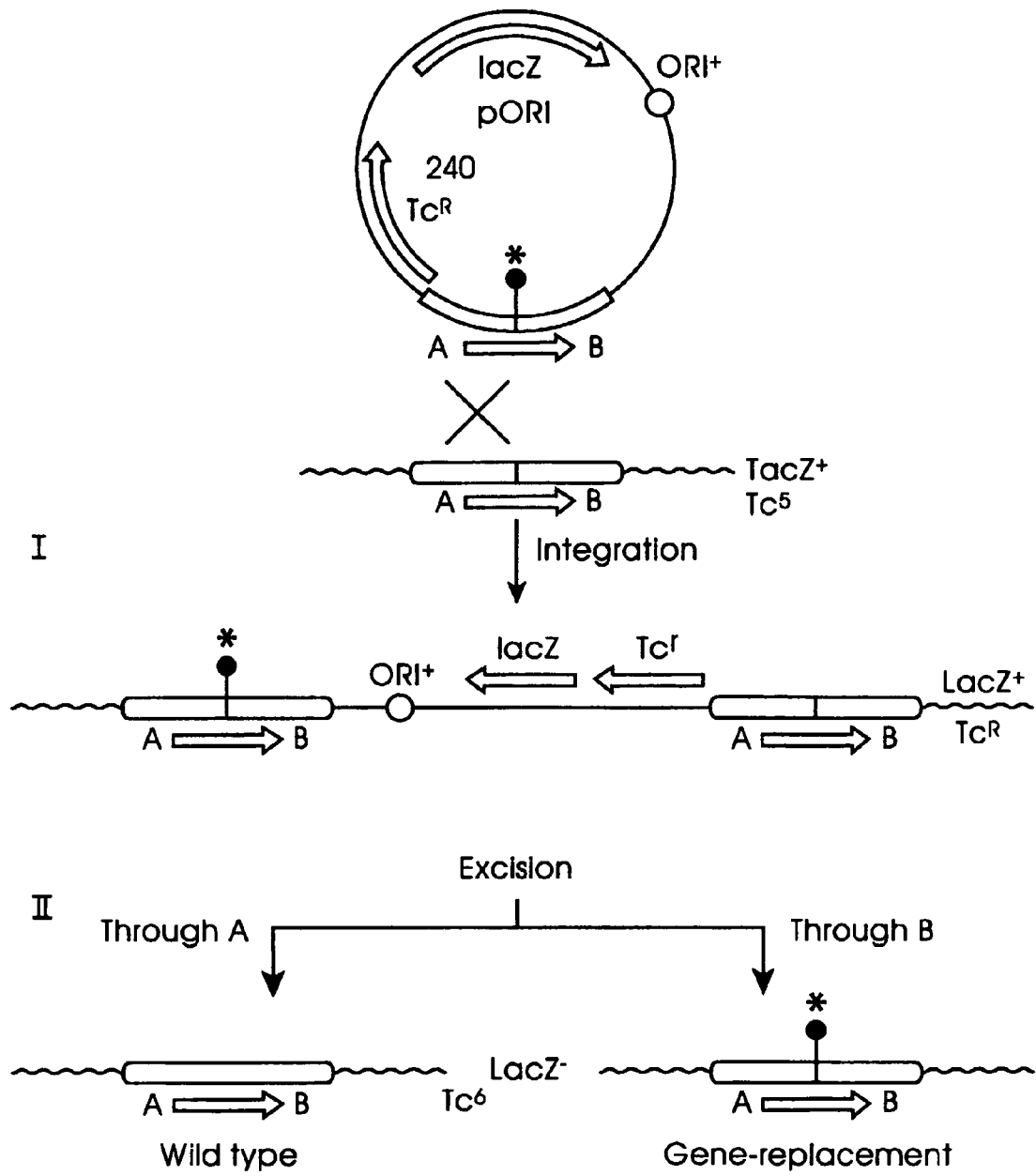

FIG. 2 illustrates the strategy for gene deletion using pORI240, where the * symbol represents the deletion of the target gene (adapted from Leenhouts et al.). Using this method, either the wild type gene is restored, or the deleted copy is inserted in its place upon resolution of the integrated plasmid.

Revertant clones can be screened out genotypically by PCR to confirm the deletion. Loss of protease activity may be confirmed phenotypically using Zymogram gele analysis (Novex) to confirm the loss of protease activity.

Other strategies for producing gene deletions can be employed.

Once an asporogenic strain, which is also protease deficient, has been prepared, it can be transformed using conventional methods, so that it expresses a gene of choice, and in particular a heterologous gene. Although particularly suited to the expression of antigens or proteins useful as vaccines such as PA of B. anthracis as described above, or immunogenic fragments or domains or variants thereof, it can be used as a expression vehicle for a wide range of proteins. It may be particularly useful where the more conventional expression hosts such as *E. coli*, are unsuited to expression of a particular target gene for example for reasons of toxicity of the protein to the *E. coli*.

Thus in a further aspect, the invention provides a recombinant asporogenic strain of *B. subtilis* as described above, which has been transformed such that it contains a heterologous gene arranged such that the gene expressed.

As mentioned above, the heterologous gene may encode a wide range of desired proteins, for example pharmaceutical or agrochemical proteins or peptides, or other proteins which have commercial applications such as enzymes, for example cellulases and amylases, used in paper manufacture or detergent manufacture. One particular form or pharmaceutical protein will be immunogenic proteins or peptides such as antigens, intended for use as a vaccine. Another form may be hormones such as human growth hormone.

A particularly preferred heterologous gene encodes PA of *B. anthracis* as described above, or immunogenic fragments, or a variant of any of these, which produce a protective immune response.

As used herein, the term "variant" refers to sequences of amino acids which differ from the base sequence from which they are derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide. Suitably variants will be at least 60% identical, preferably at least 75% identical, and more preferably at least 90% identical to the base sequence.

In particular, the identity of a particular sequence to the sequence on which they are based may be assessed using the multiple alignment method described by Lipman and Pearson, (Lipman, D. J. & Pearson, W. R. (1985) Rapid and Sensitive Protein Similarity Searches, Science, vol 227, pp1435-1441). The "optimised" percentage score should be calculated with the following parameters for the Lipman-Pearson algorithm:ktup=1, gap penalty=4 and gap penalty length=12. The sequences for which similarity is to be assessed should be used as the "test sequence" which means that the base sequence for the comparison, such as the sequence of PA of *B. anthracis* should be entered first into the algorithm.

The term "fragment" as used herein refers to truncated regions which lack one of more amino acids as compared to the full length sequence, but which produce a protective immune response. They may comprise domains.

Particular protective domains of the PA of *B. anthracis* comprise domains 1 or 4 of the full length sequence, or protective regions of these domains. These domains comprise the following sequences shown in the following Table 1.

TABLE 1

| Domain | Amino acids of full-length PA* |
|---|---|
| 4 | 596-736 |
| 1 | 1-258 |

These amino acids numbers refer to the sequence as shown in Welkos et al. Gene 69 (1988) 287-300. Domain 1 comprises two regions, designated 1a and 1b. Region 1a comprises amino acids 1-169 whereas region 1b is from amino acid 170-258. It appears that region 1a is important for the production of a good protective response.

In a particularly preferred embodiment, a combination of domains 1 and 4, or protective regions thereof, are used as the immunogenic reagent which gives rise to an immune response protective against *B. anthracis*. This combination, for example as a fusion peptide, may be expressed using the expression system of the invention.

In a further aspect, the invention comprises a method for producing a target protein, said method comprising transforming a recombinant asporogenic strain of *B. subtilis* as described above which a nucleotide sequence which encodes said protein, culturing said transformed strain and recovering said target protein from the culture.

Conventional methods, such as are generally used for the transformation and culture of microorganisms are suitably employed.

The invention will now be particularly described by way of example with reference to the accompanying diagrammatic drawings in which FIG. 1 illustrates a strategy for producing a locus for use in gene deletion; and FIG. 2 illustrates the strategy for gene deletion using pORI240.

EXAMPLE 1

Construction of a Protease-Deficient Asporogenic Strain of *Bacillus Subtilis* 168

The gene encoding the sigma factor, spoIIAC, was amplified using PCR, together with upstream flanking DNA encoding both spoIIAA and spoIIAB and downstream flanking DNA. The resultant 2.663 kb segment of DNA was synthesised by the method of Higuchi et al., Nucl. Acids Res. (1988), 16, 7351, to contain a XhoI restriction endonuclease site. This site was located 460 bp into the 760 bp spoIIAC gene. The PCR fragment was cloned into the general cloning vector pGEM3Zf (Promega) creating the plasmid pAUS-Y.

Two subsequent plasmids were constructed from the pAUS-Y by digestion and insertion of an erythromycin resistance cassette (erm) from the plasmid pDG646 (Guérot-Fleury et al., 1995. Gene, 167: 335). The first of these plasmids, pDINGO, was made by digesting pAUS-Y with XhoI and inserting a XhoI digested erm fragment. The second plasmid, pREEF, was made by digesting pAUS-Y with XHoI and ClAI to remove the last 90 bp of spoIIAB and the first 460 bp of spoIIAC. A SalI/ClaI digested erm fragment was inserted.

Both plasmids were linearised by digestion with ScaI and the DNA was then used to transform competant cells of *B. subtilis* WB600. Transformed clones were selected with erythromycin/lincomycin and genomic DNA isolated from these clones was analysed by Southern hybridisation. Digoxigenein-labelled DNA probes from the spoIIAC::erm locus were used to identify clones which contained an erm containing allelic replacement of spoIIAC.

The insertion of DNA into genes using this technique has been found to be stable and non-reverting. No reversion, (measured by the absence of spore formation) was encountered with the spoIIAC::erm strains.

EXAMPLE 2

Production of Protease Deficient Strains of *B. Subtilis*

A series of primers suitable from the construction of a protease-deficient asporogenic strain of *Bacillus subtilis* 168, using the method outlined in FIG. 1.

Specifically, the primers were designed to amplify the 5' and 3' regions flanking the gene to be deleted. The external primers (5XBA and 3XBA) are 25-26 nucleotides and incorporate an XbaI site at the 5' end. The internal primers (5XHO and 3XHO) are 41-43 nucleotides in length with target site homology on their 3' end only, then a XhoI site, then a 5' end with homology to the other primer, not to the target site. The 24 protease gene deletion primers are shown below 5'-3'.

```
APRE5XBA (25 nt);
GCTTCTAGATGAAGCCAATATTCCG          (SEQ ID NO 1)

APRE5XHO (43 nt)
TATACCTAAATAGAGCTCCATACCTGCTTCTTTTAT (SEQ ID NO 2)
TTGTCAG

APRE3XHO (41 nt)
GAAGCAGGTATGGAGCTCTATTTAGGTATATCATCT (SEQ ID NO 3)
CTCGC

APRE3XBA (25 nt)
AAGTCTAGAAATAACGTTGACATTC          (SEQ ID NO 4)

BPR5XBA (25 nt)
TCCTCTAGAAACATCACTGGAGGAC          (SEQ ID NO 5)

BPR5XHO (42 nt)
TCTGCTTAATTTCTCGAGAACATCGCTGTATATTAA (SEQ ID NO 6)
CTGTAG

BPR3XHO (42 nt)
TACTGCGATGTTCTCGAGAAATTAAGCAGATTTCCC (SEQ ID NO 7)
TGAAAA
```

BPR3XBA (25 nt)
GCTTCTAGATGGCTTCCAATGGGTC           (SEQ ID NO 8)

EPR5XBA (26 nt)
ACCTCTAGATTTCGGTTGAAAACAAG          (SEQ ID NO 9)

EPR5XHO (43 nt)
AGTATGAAAAGCCTCGAGGAAATTTTCCAAATGAAT (SEQ ID NO 10)
TTGTAAG

EPR3XHO (42 nt)
TTGGAAAATTTCCTCGAGGCTTTTCATACTATTGCT (SEQ ID NO 11)
ATACAG

EPR3XBA (25 nt)
TGTTCTAGACACGAGGTCGAGCATT           (SEQ ID NO 12)

MPR5XBA (26 nt)
ATTTCTAGAGCCGATCGGTCATGTGC          (SEQ ID NO 13)

MPR5XHO (41 nt)
CCCCTTAGCATCCTCGAGGTTTCTGATTCTTATGAT (SEQ ID NO 14)
AAAAC

MPR3XHO (43 nt)
AGAATCAGAAACCTCGAGGATGCTAAGGGGCTGCCG (SEQ ID NO 15)
GTCGAAG

MPR3XBA (25 nt)
CCGTCTAGATGTGCCGTCCAAGTCC           (SEQ ID NO 16)

NPRB5XBA (26 nt)
GACTCTAGACATCTGCCGCTGGCTTG          (SEQ ID NO 17)

NPRB5XHO (43 nt)
TGTTTTTGTTTGCTCGAGATATTTCGCTCTGCCCTT (SEQ ID NO 18)
CTTTTTC

NPRB3XHO (42 nt)
AGAGCGAAATATCTCGAGCAAACAAAAACAGTCAGG (SEQ ID NO 19)
ACACAG

NPRB3XBA (25 nt)
CGATCTAGAATTCGAAGATGCAGTC           (SEQ ID NO 20)

NPRE5XBA (25 nt)
GAATCTAGAAAGTATCCAGTCCCGC           (SEQ ID NO 21)

NPRE5XHO (41 nt)
TTTTGTTGAGTACTCGAGACAGAAAACCGCTCCTGA (SEQ ID NO 22)
TTTGC

NPRE3XHO (41 nt)
GCGGTTTTCTGTCTCGAGTACTCAACAAAAACTAAC (SEQ ID NO 23)
ATAAC

NPRE3XBA (26 nt)
GCATCTAGACAAGCAGTCCGATAATC          (SEQ ID NO 24)

PCR followed by ligation or treatment as outlined above and summarised in FIGS. 1 and 2, using some or all of the above sets of primers will result in a protease deficient strain of *B. subtilis*.

The process can either be repeated with appropriate primers to delete the spoIIAC gene, or the strategy outlined in Example 1 can be repeated to yield an asporogenic strain. The deletions can be carried out in any order.

---

The invention claimed is:

1. A recombinant microorganism comprising an asporogenic strain of Bacillus subtilis in which six genes that encode protease enzyme, namely, serine alkaline protease E (aprE), bacillopeptidase F (bpf), extracellular serine protease (epr), extracellular metalloprotease (mpr), extracellular neutral protease (nprB) and extracellular neutral metalloprotease (nprE), have been downregulated or inactivated, and wherein inactivation of a gene encoding sigma factor spoIIAC causes the strain to be asporogenic.

2. The recombinant microorganism of claim 1 wherein the protease enzyme encoding genes are deleted.

3. The recombinant microorganism of claim 1 wherein the gene encoding sigma factor spoIIAC is deleted in a sufficient amount such that the deletion of the gene encoding sigma factor spoIIAC causes the recombinant microorganism to be asporogenic.

4. The recombinant microorganism of claim 1 wherein the Bacillus subtilis is B. subtilis 168 having a mutation that causes down regulation or inactivation of a protease enzyme.

5. The recombinant microorganism of claim 1, which has been transformed with a heterologous gene, the gene being arranged to be expressed by the recombinant microorganism.

6. The recombinant microorganism of claim 5 wherein said heterologous gene encodes antigens or proteins useful in the production of a protective immune response to a pathogen.

7. The recombinant microorganism of claim 6 wherein said heterologous gene encodes protective antigen of B. anthracis or one or more of domains 1 and 4 or protective regions thereof, of the full length sequence.

8. A method for producing a target protein, said method comprising transforming a recombinant microorganism of claim 1 with a nucleotide sequence which encodes said protein, culturing said transformed strain and recovering said target protein from the culture.

9. The recombinant microorganism of claim 1, wherein the gene encoding sigma factor spoIIAC has been subject to insertion mutagenesis, such that the recombinant microorganism is asporogenic.

10. The recombinant microorganism of claim 1, wherein the gene encoding sigma factor spoIIAC has been totally deleted.

11. The recombinant microorganism of claim 1, wherein the gene encoding sigma factor spoIIAC has been deleted and has been subject to insertion mutagenesis, such that the recombinant microorganism is asporogenic.

12. The recombinant microorganism of claim 1 wherein the protease enzyme encoding genes are inactivated.

13. The recombinant microorganism of claim 1 wherein the Bacillus subtilis strain is B. subtilis 168.

14. An expression system for production of a heterologous protein, wherein said expression system comprises a recombinant asporogenic strain of Bacillus subtilis in which six genes that encode protease enzyme, namely, serine alkaline protease E (aprE), bacillopeptidase F (bpf), extracellular serine protease (epr), extracellular metalloprotease (mpr), extracellular neutral protease (nprB) and extracellular neutral metalloprotease (nprE), have been downregulated or inactivated, and wherein inactivation of a gene encoding sigma factor spoIIAC causes the strain to be asporogenic.

15. The expression system of claim 14, wherein the protease enzyme encoding genes are deleted.

16. The expression system of claim 14, wherein the gene encoding sigma factor spoIIAC is deleted in a sufficient amount such that the deletion of the gene encoding sigma factor spoIIAC causes the expression system to be asporogenic.

17. The expression system of claim 14, wherein the Bacillus subtilis is B. subtilis 168, having a mutation that causes down regulation or inactivation of at least one protease enzyme.

18. The expression system of claim 14, which has been transformed with a heterologous gene, the gene being arranged to be expressed by the recombinant microorganism.

19. The expression system of claim 14, wherein the heterologous gene encodes antigens or proteins useful in the production of a protective immune response to a pathogen.

20. The expression system of claim 14, wherein the heterologous gene encodes protective antigen of B. anthracis or one or more of domains 1 and 4 or protective regions thereof of the full length sequence.

* * * * *